United States Patent
Nakanishi

Patent Number: 5,252,065
Date of Patent: Oct. 12, 1993

[54] CARTRIDGE TYPE DENTAL HANDPIECE

[75] Inventor: Takasuke Nakanishi, Kanuma, Japan

[73] Assignee: Nakanishi Dental Mfg. Co., Ltd., Tochigi, Japan

[21] Appl. No.: 926,759

[22] Filed: Aug. 7, 1992

[30] Foreign Application Priority Data

Aug. 12, 1991 [JP] Japan .................. 3-201864

[51] Int. Cl.⁵ .................. A61C 1/08; A61C 1/10; A61C 1/12; A61C 1/05
[52] U.S. Cl. .................. 433/126; 433/82; 433/115
[58] Field of Search .......... 433/103, 104, 115, 126, 433/127, 128, 129, 82

[56] References Cited

U.S. PATENT DOCUMENTS

| | | | |
|---|---|---|---|
| 4,234,308 | 11/1980 | Leonard | 433/127 |
| 4,369,034 | 1/1983 | Garnier et al. | 433/115 |
| 4,975,056 | 12/1990 | Eibofner | 433/84 |
| 5,078,601 | 1/1992 | Badoz et al. | 433/82 |
| 5,167,501 | 12/1992 | Castellini | 433/82 |

Primary Examiner—Gene Mancene
Assistant Examiner—Cindy A. Cherichetti
Attorney, Agent, or Firm—Darby & Darby

[57] ABSTRACT

A cartridge type dental handpiece contains a handpiece main body, a head housing provided at a distal end of the handpiece main body, and a cartridge detachably adapted within the head housing. The cartridge has a cartridge casing and a rotatable sleeve rotatably mounted within the cartridge casing and adapted for detachably holding a dental burr. The dental handpiece further contains a fluid passage defined between an inner surface of the head housing and an outer surface of the cartridge casing when the cartridge is mounted within the head housing, a fluid spraying port formed in a lower surface of the cartridge casing in communication with the fluid passage for spraying the fluid from the fluid passage onto a tooth being treated, and a communication port for supplying the fluid from a fluid supply duct within the handpiece main body into the fluid supply passage.

6 Claims, 3 Drawing Sheets

CARTRIDGE TYPE DENTAL HANDPIECE

BACKGROUND OF THE INVENTION

This invention relates to a dental handpiece. More particularly, it relates to a cartridge type dental handpiece in which a cartridge for receiving and securing a dental burr is removably attached to a head housing provided at a distal end of the handpiece.

There have hitherto been employed a variety of so-called cartridge type dental handpieces in which a burr sleeve for secrring a dental burr and bearings for rotatably holding the burr sleeve are housed within a cartridge which is removably attached to a head housing provided at the distal end of the handpiece. The dental handpiece is provided with a spray unit for spraying a cooling fluid, such as water or air to a site of treatment for cooling the site during tooth cutting. In conventional cartridge type dental handpieces, such spraying units as shown in FIGS. 3 and 4 are employed. In an example shown in FIG. 3, air, water or a mixture thereof is sprayed to the site of treatment via an air supply port 52 and a water supply port 53 provided in the handpiece main body and communicating with an air-supply channel 50 and a water-supply channel 51, respectively. In an example shown in FIG. 4, the lower end face of the head housing 55 is planar and a front cap 57 having a recess or groove is mounted in intimate contact with the planar lower end surface of the head housing 55 for establishing an annular fluid passage 56 to which air and water are supplied via an air-supply port 52 and a water-supply port 53 opened on the lower end surface of the head housing 55 so as to be sprayed via fluid ejecting ports 58, 59 provided at predetermined positions within the fluid passage 56.

However, the conventional spray unit shown in FIG. 3, while having an advantage that the head is neat in appearance so that the site of treatment may be viewed more easily, is disadvantageous in that the opening positions of the air-supply port 52 and the water-supply port 53 are remote from a dental burr 60, while the fluid can be sprayed only in one direction proceeding from the handpiece main body to the site of treatment, so that the cooling effect is diminished, with the fluid being unable to reach the site of treatment particularly when cutting the lateral side of the tooth or cutting through the inside of the tooth.

While the conventional spray unit shown in FIG. 4 has an advantage that the fluid may be sprayed from many directions by providing plural fluid ejecting ports 58, 59 along the fluid passage 56, and spraying may be made from positions close to the site of treatment with improved cooling effects, the spray unit raises a problem that the field of view is interrupted during treatment by an enlarged lower head end, while the operation of attaching the front cap 57 to the lower end face of the head housing 55 in intimate contact therewith cannot be achieved without considerable difficulties.

SUMMARY OF THE INVENTION

It is therefore an object of the present invention to provide a cartridge type dental handpiece in which the fluid may be sprayed from many directions from a position close to the site of treatment, in which the field of view is interrupted only to a lesser extent during treatment and in which a spray unit may be constituted and dismounted easily by attachment or detachment of the cartridge with respect to the head housing and the handpiece main body.

It is another object of the present invention to provide a cartridge type dental handpiece in which impurities such as debris of cut teeth may be prevented from being intruded into the cartridge.

According to the present invention, there is provided a cartridge type dental handpiece comprising a handpiece main body, a head housing provided at the distal end of the handpiece main body and a cartridge detachably adapted within the head housing, the cartridge having a cartridge casing and a rotatable sleeve rotatably mounted within the cartridge casing and adapted for detachably holding a dental burr, the dental handpiece further comprising a fluid passage defined between the inner surface of the head housing and the outer surface of the cartridge casing when the cartridge is mounted within the head housing, a fluid spraying port formed in the lower surface of the cartridge casing in communication with the fluid passage for spraying the fluid from the fluid passage onto a tooth being treated and a communication port for supplying the fluid from a fluid supply duct within the handpiece main body into the fluid supply passage.

PREFERRED EMBODIMENT OF THE INVENTION

Figure 1:
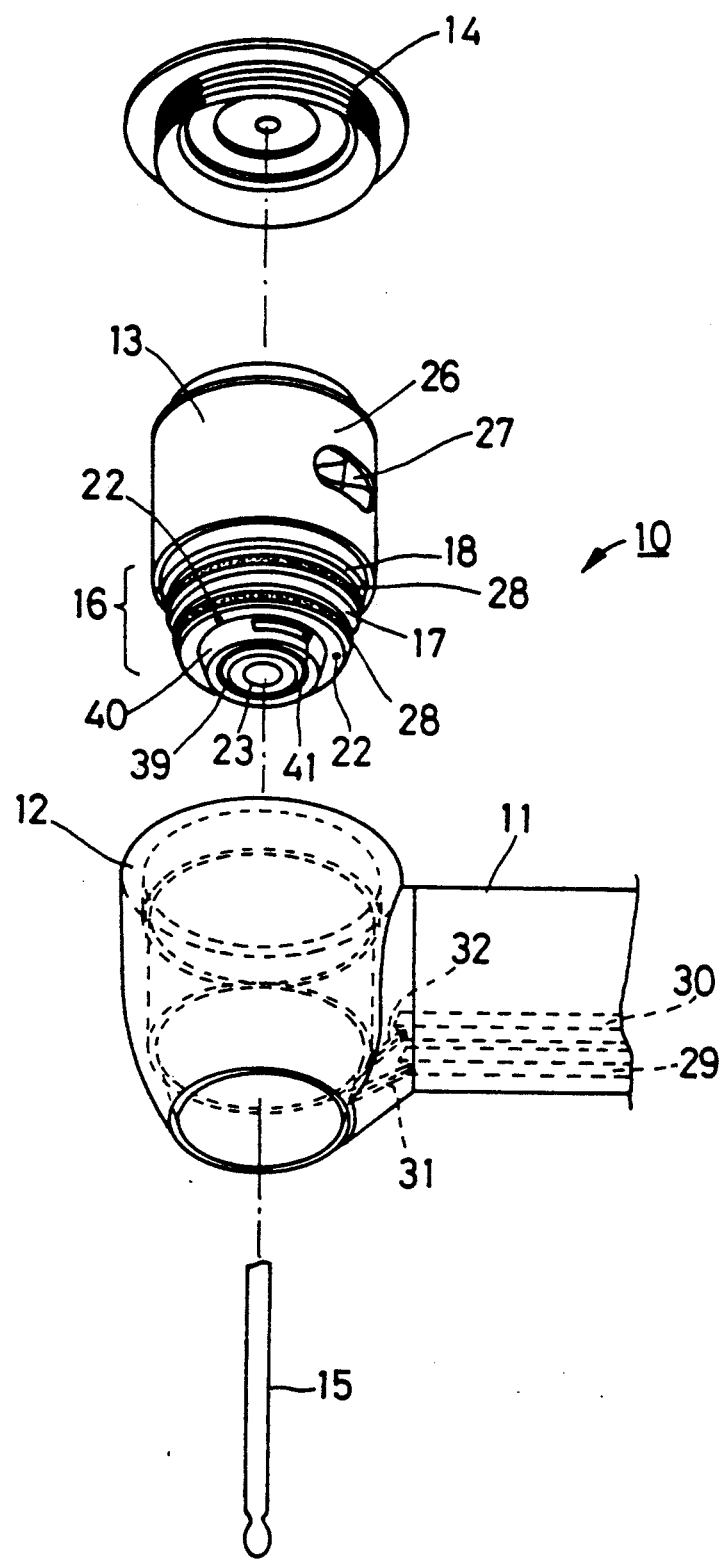
FIG. 1 is an exploded perspective view showing essential parts of a dental handpiece according to an embodiment of the present invention.

Referring to FIG. 1, a dental handpiece 10 of the present embodiment includes a head housing 12 attached to the distal end of a handpiece main body 11, and a cartridge 13 attached to the head housing 12. When the dental handpiece 10 is used, the cartridge 13 is threadedly secured in position within the head housing 12 by a head cap 14, and a dental tool or burr 15 is inserted into and secured to the lower end of the cartridge 13.

Figure 2:
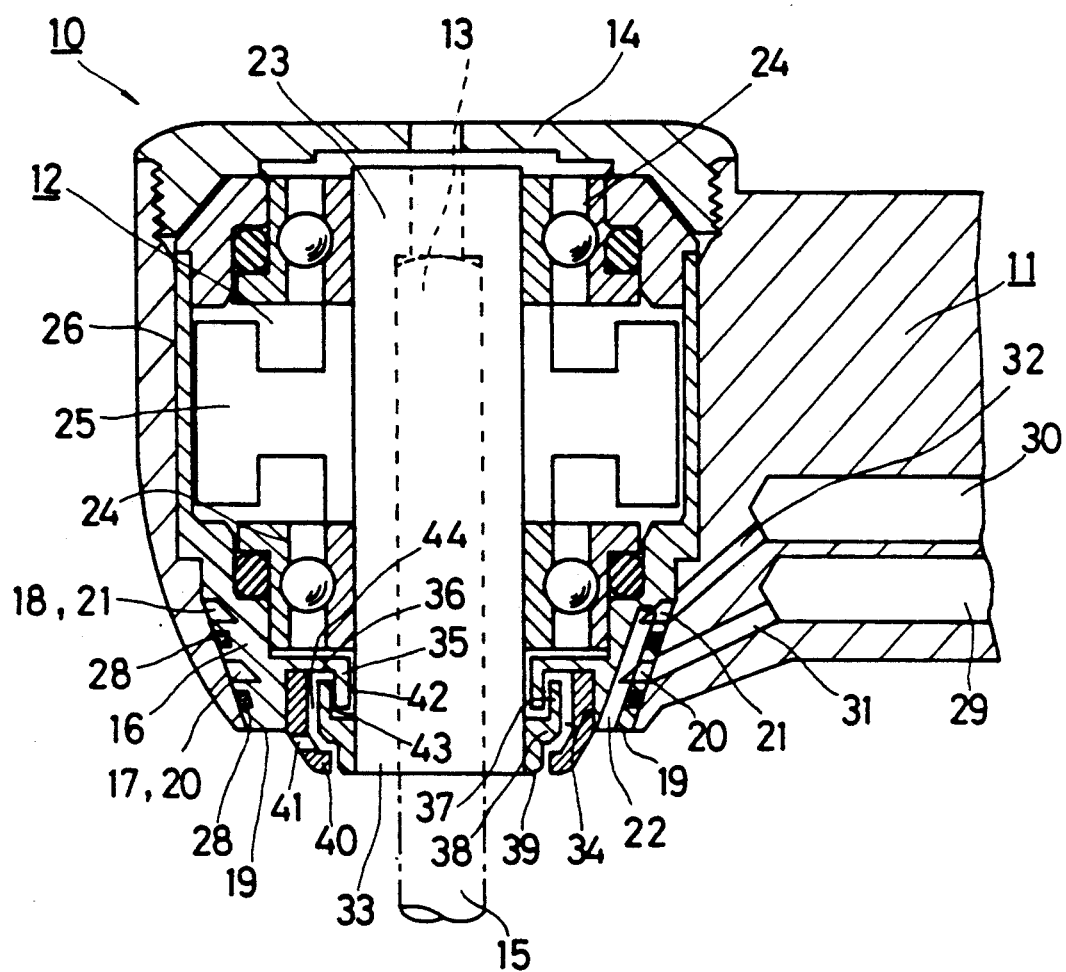
FIG. 2 is a detailed cross-sectional view of the embodiment shown in FIG. 1.
Figure 3:
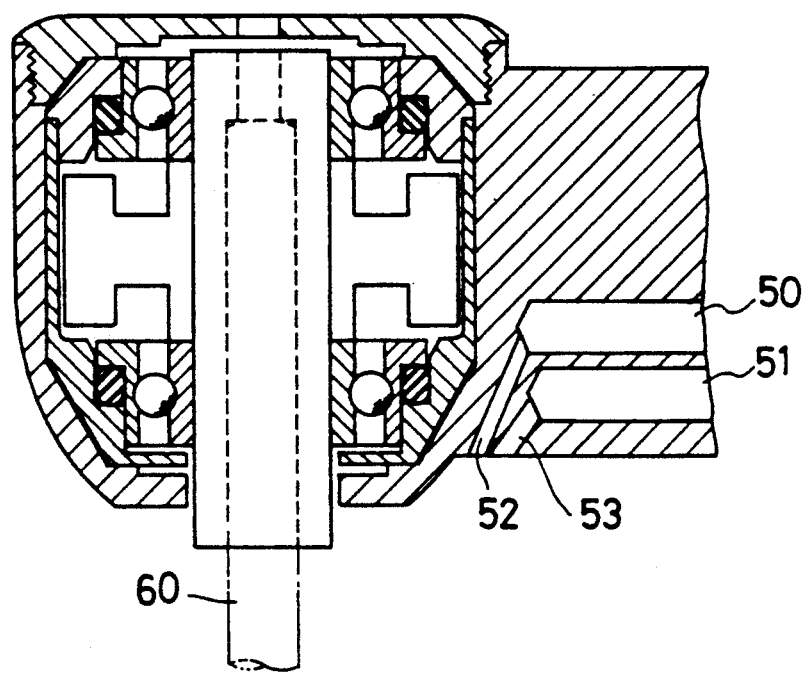
FIG. 3 is a cross-sectional view showing an embodiment of a spray mechanism of a conventional dental handpiece.
Figure 4:
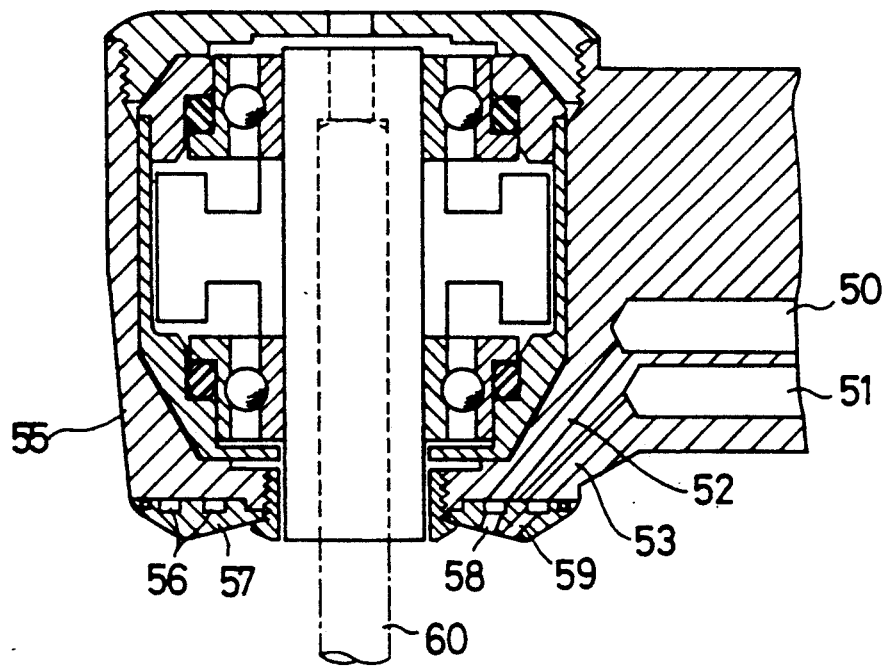
FIG. 4 is a cross-sectional view showing another embodiment of a spray mechanism of a conventional dental handpiece.

The cartridge 13 is a cylinder having a frusto-conical lower inclined or tapered part 16. An annular water-supply groove 17 and an annular air-supply groove 18 are formed on an outer peripheral surface of the tapered part 16, and two O-rings 28 are mounted on the outer peripheral surface on both sides of the water-supply groove 17. Referring to FIG. 2, the cartridge 13 is secured to the head housing 12 so that the tapered part 16 thereof is intimately contacted with the inner inclined surface of the head housing 12 under the thrusting force exerted by the head cap 14 with an end face 19 of the cartridge 13 being projected and exposed from the lower end of the head housing 12. As a result thereof, an annular water-supply channel 20 and an annular air-supply channel 21 are defined between the water-supply groove 17 and the air-supply groove 18 provided in the inclined part 16 on one hand and the inner peripheral surface of the head housing 12 on the other hand, respectively. The O-rings 28 are brought into tight contact with the inner peripheral surface of the head housing 12 to prevent water leakage from the water-supply channel 20. Three spray ports 22, 22, 22 communicating with the channels 20, 21 are formed so as to be opened on the lower end face 19 of the cartridge 13 at an angular interval of about 120° from one another along the periphery of the outer end face 19 of the cartridge 13.

The cartridge 13 of the present embodiment includes a pneumatic rotating mechanism, and is provided with a burr sleeve 23 for receiving and securing the dental tool or burr 15, upper and lower ball bearings 24, 24 for rotationally holding the burr sleeve 23, a rotor 25 secured to the outer periphery of the burr sleeve 23 between the upper and lower bearings 24, 24 and a cartridge casing 26 for accommodating these cartridge components. The burr sleeve 23 is rotationally driven under the force of air flowing via an aperture 27 (FIG. 1) provided in the outer periphery of the cartridge casing 26.

On the other hand, the handpiece main body 11 is provided with a water-supply communication port 31 and an air-supply communication port 32 for supplying water and air from a water-supply duct 29 and an air-supply duct 30 within the handpiece main body 11, respectively, to the water-supply channel 20 and the air-supply channel 21, respectively. These communication ports 31, 32 are previously formed in the cartridge main body 11 to be opened in the inner peripheral surface of the head housing 12 at positions in register with the water-supply channel 20 and the air-supply channel 21, respectively, when the cartridge 13 is mounted in position relative to the handpiece main body 11 and the head housing 12.

In the above-described dental handpiece 10, water and air supplied from the water-supply duct 29 and the air-supply duct 30 during dental treatment are supplied via communication ports 31, 32 to the annular water-supply channel 20 and the annular air-supply channel 21, respectively. Water and air or a mixture thereof are sprayed onto a site of treatment from three directions via three spray ports 22 surrounding the burr sleeve 23 and from positions proximate to the dental tool 15 mounted on the burr sleeve 23.

The handpiece 10 of the present embodiment also includes a dust- and water-proofing mechanism for preventing impurities, such as debris of cut tooth or water droplets, from being intruded into the inside of the cartridge 13. That is, the lower end 33 of the burr sleeve 23 passes through the lower end face of the cartridge casing 26 and forms an opening 34 concentric with the burr sleeve 23 and spaced from the burr sleeve 23. At the base part of the opening 34, which is spaced apart from the outer periphery of the burr sleeve 23, there is provided a stationary partitioning member 36 having an L-shaped cross-section. The partitioning member 36 is extended radially inwardly from the inner peripheral surface of the opening 34 and then extended downwardly a predetermined distance as a lower extension 35 in a state free from contact with the burr sleeve 23. A dust-proofing disc 39 defining a rotatable partitioning member 38 having an L-shaped cross-section is secured to the outer peripheral surface of the lower end 33 of the burr sleeve 23. The disc 39 is extended radially outwardly from the lower end 33 and then extended upwardly in the form of an upper extension 37, a part of which is arranged between the lower extension 35 of the stationary partitioning member 36 and the inner peripheral surface of the opening 34 in a non-contact state. A disc cover 40 is mounted in contact with the inner peripheral surface of the opening 34 and extended a predetermined distancee from the lower end of the opening 34 for covering the dust-proofing disc 39 in a non-contact state. Discharge holes 41 are formed in the extended part of the disc cover 40 at predetermined circumferential distances from one another. The result is that, at a lower region of the burr sleeve 23, the burr sleeve 23, the lower extension 35 of the stationary partitioning member 36, the upper extension 37 of the rotatable partitioning member 38 and the disc cover 40 are arranged concentrically such that first to third gaps 42, 43 and 44 are defined between the burr sleeve 23 and the lower extension 35, between the lower extension 35 and the upper extension 37 and between the upper extension 37 and the disc cover 40, in communication with one another, respectively.

In the operation of the dental handpiece 10, since the radii of the burr sleeve 23, and the inner peripheral surface and the outer peripheral surface of the upper extension 37 of the rotatable partitioning member 38 are increased in this order with rotation of the burr sleeve 23, the flow velocities of air in the first gap 42, the second gap 43 and the third gap 44 are increased in this order, as a result of which the pneumatic pressure becomes lowest within the third gap 44 to cause impurities such as debris to be introduced into the third gap 44 as well as to prevent the impurities from being intruded into the second gap 43 and the first gap 42 where higher pneumatic pressures are maintained. The impurities introduced into the third gap 44 are discharged to outside via discharge holes 41 in the disc cover 40 under the centrifugal force.

Although the present invention has been described with reference to the preferred embodiment, it should be understood that various modifications and variations can be easily made by those skilled in the art without departing from the spirit of the invention. Accordingly, the foregoing disclosure should be interpreted as illustrative only and is not to be interpreted in a limiting sense. The present invention is limited only by the scope of the following claims.

What is claimed is:

1. A cartridge type dental handpiece comprising a handpiece main body, a head housing provided at a distal end of said handpiece main body, and a cartridge detachably adapted within said head housing, said cartridge having a cartridge casing and a rotatable sleeve rotatably mounted within said cartridge casing and adapted for detachably holding a dental burr, the dental handpiece further comprising a fluid passage defined between an inner surface of the head housing and an outer surface of the cartridge casing when the cartridge is mounted within said head housing, a fluid spraying port formed in a lower surface of said cartridge casing in communication with said fluid passage for spraying the fluid from said fluid passage onto a tooth being treated, and a communication port for supplying the fluid from a fluid supply duct within said handpiece main body into said fluid supply passage.

2. The dental handpiece according to claim 1 further comprising a rotatable partitioning member provided in vicinity of a lower end of said rotatable sleeve, said rotatable partitioning member being extended radially outwardly from said rotatable sleeve and then extended axially in the form of a rotatable extension, and a stationary partitioning member provided in vicinity of a lower end of said cartridge casing, said stationary partitioning member being spaced apart radially outwardly from said rotatable partitioning member, said stationary partitioning member having a stationary extension facing to and spaced apart radially inwardly from said rotatable extension, an outer surface of said rotatable sleeve and said stationary extension defining a first gap, said stationary extension and said rotatable extension defining a second gap communicating with said first gap, said rotatable extension and an inner surface of said stationary partitioning member defining a third gap communicating with said second gap, said stationary partitioning member having a debris discharge hole for establishing communication of said third gap with outside air.

3. The dental handpiece according to claim 1 wherein an outer surface of said cartridge casing has a groove as said fluid passage.

4. The dental handpiece according to claim 1 wherein said fluid passage comprises an air-supply passage and a water-supply passage.

5. The dental handpiece according to claim 1 wherein an outer surface of said cartridge casing is formed with an air-supply groove and a water-supply groove as said fluid passage.

6. The dental handpiece according to claim 1 wherein said rotatable extension is extended axially upwardly and said stationary extension is extended axially downwardly.

* * * * *